US010730820B2

(12) United States Patent
Tothadi et al.

(10) Patent No.: US 10,730,820 B2
(45) Date of Patent: Aug. 4, 2020

(54) SOLID POROUS FORM OF TRIMESIC ACID AND A PROCESS FOR PREPARATION THEREOF

(71) Applicant: COUNCIL OF SCIENTIFIC AND INDUSTRIAL RESEARCH, New Delhi (IN)

(72) Inventors: Srinu Tothadi, Maharashtra (IN); Rahul Banerjee, Maharashtra (IN)

(73) Assignee: COUNCIL OF SCIENTIFIC AND INDUSTRIAL RESEARCH (IN)

( * ) Notice: Subject to any disclaimer, the term of this patent is extended or adjusted under 35 U.S.C. 154(b) by 0 days.

(21) Appl. No.: 16/401,664

(22) Filed: May 2, 2019

(65) Prior Publication Data

US 2019/0337879 A1 Nov. 7, 2019

(30) Foreign Application Priority Data

May 2, 2018 (IN) .............................. 201811016542

(51) Int. Cl.
*C07C 63/307* (2006.01)
*C07C 51/43* (2006.01)
*B01J 20/22* (2006.01)

(52) U.S. Cl.
CPC ............. *C07C 63/307* (2013.01); *B01J 20/22* (2013.01); *C07C 51/43* (2013.01); *C07B 2200/13* (2013.01); *C07C 2601/16* (2017.05)

(58) Field of Classification Search
CPC ...................................................... C07C 51/43
See application file for complete search history.

(56) References Cited

FOREIGN PATENT DOCUMENTS

CN 103288632 A * 9/2013

OTHER PUBLICATIONS

Machine translation of CN103288632, 2013.*
Stefan J.H. Griess et al., "Incorporation and Manipulation of Coronene in an Organic Template Structure", Published in Langmuir, 2004, 20 (21), pp. 9403-9407 (5 total).
Nguyen Thi Ngoe Ha et al., "Polymorphs of Trimesic Acid Controlled by Solvent Polarity and Concentration of Solute at Solid-Liquid Interface", Published in journal Surface Science, 607, 2013, pp. 68-73 (Total 6).
David J. Duchamp et al., "Acta Crystallographic", Oct. 31, 1967, Only Abstract/Introduction, pp. 1.

* cited by examiner

*Primary Examiner* — Ana Z Muresan
(74) *Attorney, Agent, or Firm* — The Belles Group, P.C.

(57) ABSTRACT

The present invention relates to hexagonal hollow rods and a porous single crystalline structure, namely Form II of trimesic acid of Formula (A) and a process for preparation thereof. The present invention also discloses that the new solid porous single crystalline Form II of trimesic acid shows high adsorption for Rhodamine B (RHB) dye.

5 Claims, 12 Drawing Sheets

SOLID POROUS FORM OF TRIMESIC ACID AND A PROCESS FOR PREPARATION THEREOF

CROSS-REFERENCE TO RELATED APPLICATIONS

This application claims the benefit of Indian Patent Application 201811016542, filed May 2, 2018. The disclosure of the above application(s) is (are) incorporated herein by reference.

FIELD OF THE INVENTION

The present invention relates to a new solid porous structural form of trimesic acid of Formula (A). More particularly, the present invention relates to hexagonal hollow rods and a porous single crystalline structural form, namely Form II of trimesic acid of Formula (A) and a process for preparation thereof.

BACKGROUND AND PRIOR ART OF THE INVENTION

Trimesic acid, also known as benzene-1, 3, 5-tricarboxylic acid of Formula (A), is a benzene derivative with three carboxylic acid groups. Trimesic acid is a planar molecule. It is made up of a benzene ring with three carboxylic groups at the 1, 3, and 5 positions, and it can be synthesized from the oxidation of 1,3,5-trimethyl benzene. The acid is an important building block in crystal engineering and is used to form honeycomb structures. Trimesic acid has the ability to form diverse supramolecular structures. Also, trimesic acid salt and the free trimesic acid are useful as a plasticizer.

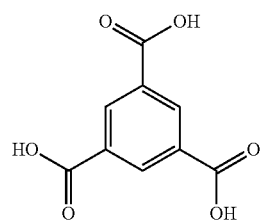

Formula (A)

Article titled "The crystal structure of trimesic acid (benzene-1,3,5-tricarboxylic acid)" by David J. Duchamp et al. published in *Acta Crystallographica* (1969) B25, 5 reports determination of the crystal structure of one modification of trimesic acid (benzene-1,3,5-tricarboxylic acid). The crystals are monoclinic, space group (2/c, with a=26.52, b=16.42, c=26.55 A° and β=91.53°; there are 48 molecules in the cell and six molecules are in the asymmetric unit. This was the first report of trimesic acid and in the crystal structure hexagonal rings are interpenetrated and crystal packing does not show any extended pores/voids. It also talks about structure determination, bond lengths and angles, temperature effect, and hydrogen bonding of the crystals.

Article titled "Incorporation and manipulation of coronene in an Organic template structure" by Stefan J. H. Griess et al. published in *Langmuir*, 2004, 20 (21), pp 9403-9407 reports a two-dimensional molecular template structure of 1, 3, 5-benzenetricarboxylic acid (trimesic acid, TMA). It was formed on a highly oriented pyrolytic graphite surface (HOPG) by self-assembly at the liquid-solid interface. Scanning tunneling microscopy (STM) investigations show high-resolution images of the porous structure on the surface. After the host structure was created, coronene molecules were inserted as guest molecules into the pores. STM results indicate that some of the guest molecules rotate inside their molecular bearing. Further investigations show that single coronene molecules can be directly kicked out of their pores by means of STM. This article is about 2D structure of trimesic acid and to observe this pattern, it requires some solid support such Cu (100) in UHV (Ultra High Vacuum) and it was not about isolation of single crystals structure.

The article titled "Polymorphs of trimesic acid controlled by solvent polarity and concentration of solute at solid-liquid interface" by Nguyen Thi Ngoc Ha et. al and published in the journal "*Surface Science* 607 (2013) 68-73" reports study on the crystallinity of the trimesic acid in solvents with different polarities. The article teaches that with highly polar solvents trimesic acid show a mixed pattern consisting of TMA dimer-tape embedded between alcohol lamella, with moderately polar solvents it shows well known chicken wire structure and no ordered structure with non-polar solvents.

The existing prior art do not provide other crystalline forms of the trimesic acid. The prior art documents disclose that trimesic acid exists as interpenetrated structure and no other single crystalline structural form has been reported so far for trimesic acid. While honeycomb structures in organic crystals are not common, such a structure as a single crystal of one component has not been reported.

Therefore, there is a need in the art to explore different crystalline forms of trimesic acid like honeycomb structure by considering the utility of the trimesic acid compound. Single crystal is also another such crystalline form, which does not require any templet to support the framework.

OBJECTS OF THE INVENTION

Main objective of the present invention is to provide a new solid porous structural form referred to as Form II of trimesic acid of Formula (A).

Another objective of the present invention is to provide a hexagonal hollow rods and a porous single crystalline structural form (Form II) of trimesic acid of Formula (A).

Still another objective of the present invention is to provide a process for the preparation of hexagonal hollow rods and a porous single crystalline structural form (Form II) of trimesic acid of Formula (A).

Yet another objective of the present invention is to provide a new solid porous single crystalline structural form (Form II) of the trimesic acid, wherein said Form II shows high adsorption Rhodamine B dye.

BRIEF SUMMARY

Accordingly, the present invention provides a new solid structural form (Form II) of trimesic acid of Formula (A).

In an aspect, the present invention provides hexagonal hollow rods and a porous single crystalline form of trimesic acid of Formula (A)

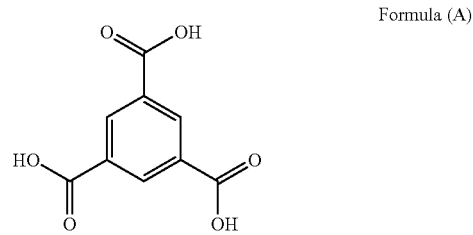 [SMILES: O=C(O)c1cc(C(=O)O)cc(C(=O)O)c1]

Formula (A)

In another aspect, the present invention provides a crystalline structural form of the trimesic acid of Formula (A) having a characteristic peaks of 2θ values at 6.2°, 10.9°, 15.5°, 15.9°, 16.6°, 19.0°, 20.9°, 21.9°, 22.5°, 22.8°, 24.4°, 27.4°, 27.9°, 29.7°, 30.3°, 31.1°, 31.9°, 33.6°, 34.4°, 37.9°, 39.1°, 39.7°, 40.7°, 42.6° for the powder X-ray diffraction.

In another aspect, the present invention provides a crystalline structural form of the trimesic acid of Formula (A) that is stable up to 150° C.

In another aspect, the present invention provides a process for the preparation of hexagonal hollow rods and a porous single crystalline structural form (Form II) of trimesic acid of Formula (A) comprising the steps of:
a) dissolving trimesic acid in a suitable solvent to obtain clear solution; and
b) evaporating the solution of step (a) at a suitable temperature for the suitable period of time to afford hexagonal hollow rods of porous single crystalline structural form (Form II) of trimesic acid.

In another aspect, the present invention provides a process for the synthesis of hexagonal hollow single crystalline structural form (Form II) of trimesic acid of Formula (A) comprising of: a) dissolving trimesic acid in an ether solvent selected from tetrahydrofuran, diethyl ether, 1,4-dioxane, methyl tert-butyl ether, and mixtures thereof to obtain a clear solution; and b) evaporating the solution of step (a).

In another aspect, the present invention provides a process for the synthesis of hexagonal hollow single crystalline structural form (Form II) of trimesic acid of Formula (A) comprising of: a) dissolving trimesic acid in a suitable solvent to obtain a clear solution; and b) evaporating the solution of step (a) at the temperature of 27° C.

In another aspect, the present invention provides a process for the synthesis of hexagonal hollow single crystalline structural form (Form II) of trimesic acid of Formula (A) comprising of: a) dissolving trimesic acid in a suitable solvent to obtain a clear solution; and b) evaporating the solution of step (a) in the temperature range of 20° C.-40° C. for 24 to 120 hours.

Yet another embodiment of the present invention provides a new solid porous single crystalline structural form (Form II) of the trimesic acid, wherein said Form II shows high adsorption Rhodamine B dye.

In another aspect, the present invention provides a crystalline structural form of the trimesic acid of Formula (A) having an 82% adsorption for Rhodamine B (RHB) dye.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

ACRONYMS USED IN THE INVENTION

TMA: Trimesic acid
HOPG: Highly oriented pyrolytic graphite surface
STM: Scanning tunneling microscopy
PXRD: Powder X-Ray Diffraction
TGA: Thermogravimetric analysis
DSC: Differential scanning calorimetry
VTSCXRD: Variable temperature single-crystal X-ray diffraction
VT PXRD: Variable temperature X-ray powder diffraction
SSNMR: Solid State Nuclear Magnetic Resonance
SEM: Scanning Electron Microscope
THF: Tetrahydrofuran
SCXRD: Single-crystal X-ray diffraction

BRIEF DESCRIPTION OF THE DRAWINGS

The present invention will become more fully understood from the detailed description and the accompanying drawings, wherein.

DETAILED DESCRIPTION

Figure 1:
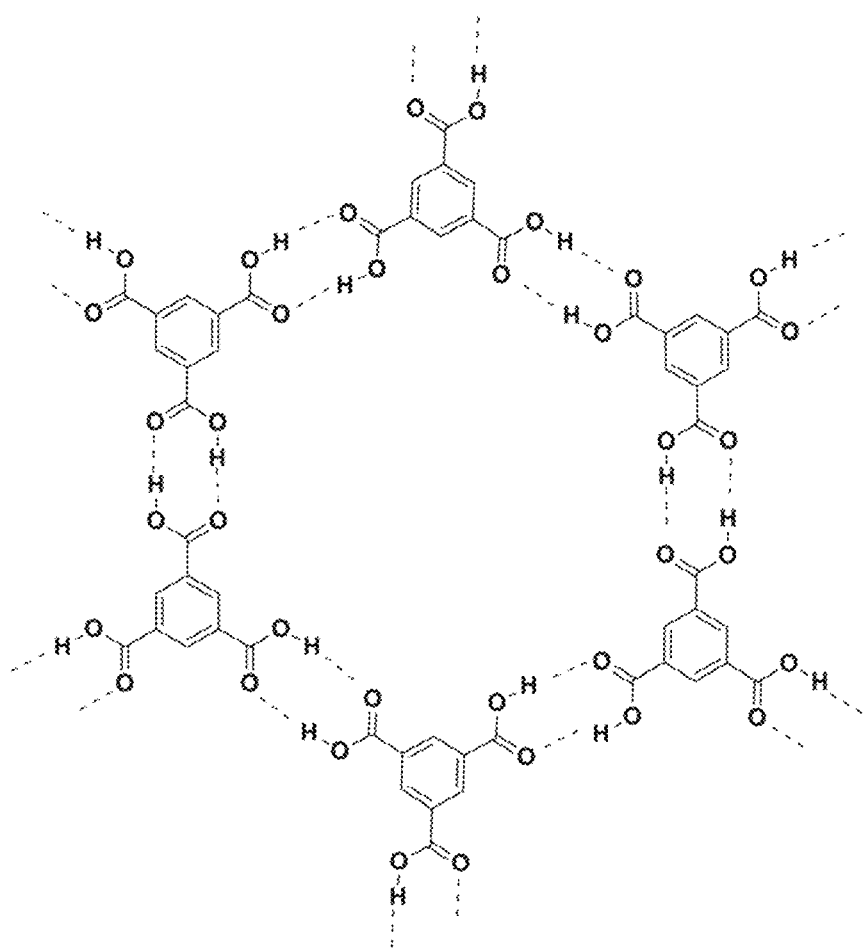
FIG. 1: Trimesic acid and basic supramolecular synthon (acid-acid dimer) in the crystal packing (Form II and Form I).

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention will now be described in detail in connection with certain preferred and optional embodiments, so that various aspects thereof may be more fully understood and appreciated.

Accordingly, the present invention provides a new solid structural form Form II of trimesic acid of Formula (A).

In an aspect, the present invention provides hexagonal hollow rods and a porous single crystalline structural form (Form II) of trimesic acid of Formula (A)

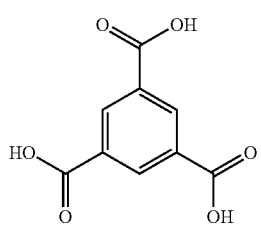

Formula (A)

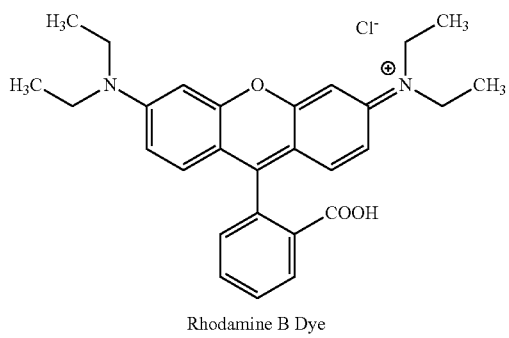 [SMILES: CCN(CC)c1ccc2c(-c3ccccc3C(=O)O)c3ccc(=[N+](CC)CC)cc-3oc2c1 ; [Cl-]]

Rhodamine B Dye

In another aspect, the present invention provides a process for the preparation of hexagonal hollow rods and a porous single crystalline structural form (form II) of trimesic acid of Formula (A) comprising the steps of:

a) dissolving trimesic acid in a suitable solvent to obtain clear solution; and b) evaporating the solution of step (a) at a suitable temperature for the suitable period of time to afford hexagonal hollow rods of porous single crystalline structural form (Form II) of trimesic acid.

Suitable solvent used to obtain clear solution at step a) may include polar solvent, non-polar solvent, ether solvent, and mixtures thereof. Suitable polar solvent may include water, ammonia, sulfuric acid, deuterium oxide, ethanol, methanol, acetone, isopropanol, methyl ethyl ketone, n-propanol, acetonitrile, DMSO, and DMF and mixtures thereof. Suitable non-polar solvents may include chloroform, pentane, hexane, benzene, toluene, octane, decane, dimethyl ether, and dichloromethane, and mixtures thereof. Suitable ether solvents include tetrahydrofuran, diethyl ether, 1,4-dioxane, methyl tert-butyl ether, and mixtures thereof. In particularly useful embodiments, ether solvents are used and most preferably tetrahydrofuran (THF) is used as a solvent in step a).

Suitable temperature at step b) for evaporation of solvent is in the range of 20-40° C. In particularly useful embodiment, temperature used at step b) is 27° C.

Suitable period of time to evaporate the solvent at step b) is 24-120 hr.

In still another embodiment, the morphology of the synthesized trimesic acid of Form II is hexagonal rods and with time, hexagonal rods convert into hexagonal hollow cylinders and crystalline material that is stable at the temperature in the range of 140° C. to 150° C.

The honeycomb single crystalline structure of trimesic acid of Form II is porous and mimicking the honeycomb pattern as a single component crystal, wherein the honeycomb pattern is the smallest honeycomb pattern (hexagon) existing in the nature.

In yet another embodiment, the synthesized trimesic acid of Form II is used in gas absorption, drug delivery and separation of mixtures of gases. The present invention provides a new solid porous single crystalline Form II of the trimesic acid, wherein said Form II shows high adsorption for Rhodamine B dye.

Rhodamine B (RHB), is a basic synthetic dye imparting a red color in aqueous solution and frequently used in textile, paper, and paint and leather industries. It usually present in the water as impurity and is removed as ion floatation. Form II of trimesic acid of the present invention adsorbs Rhodamine B (RHB) dye due to higher surface area. Hence Form II of the present invention is useful in removing Rhodamine B (RHB) dye from waste water.

Figure 5:
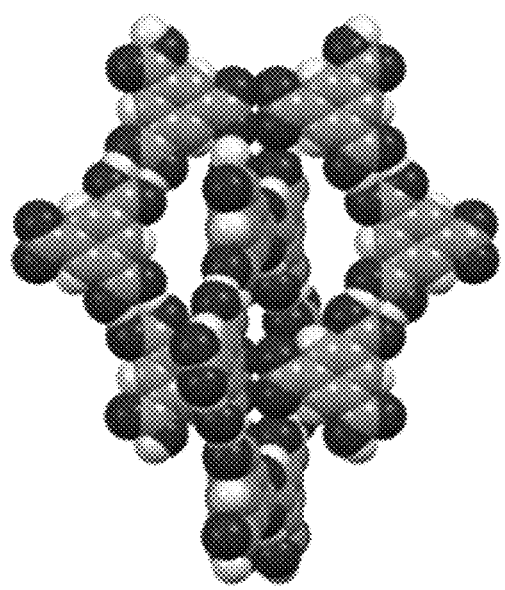
FIG. 5: Interlocked or interpenetrated structure of trimesic acid (Form I), two different hexagonal rings interpenetrated to form non-porous crystal packing.

Form I is a reported crystalline form of trimesic acid in the literature (Danid J. Duchamp, Richard E. Marsh, *Acta Cryst.* (1969), B25, 5). Characteristics of the Form II of the present invention are compared with reported Form I and are depicted by FIGS. 3 and 5 respectively.

FIG. 1 depicts trimesic acid and basic supramolecular synthon (acid-acid dimer) in the crystal packing (Form II and Form I). Six molecules of trimesic acid form hexagonal ring. It is common in both Form I and II but, Form II extends two dimensionally without interpenetration of hexagonal rings and in 3D it extends through π . . . π stacking whereas Form I interpenetrate to form non-porous crystal.

Figure 2:
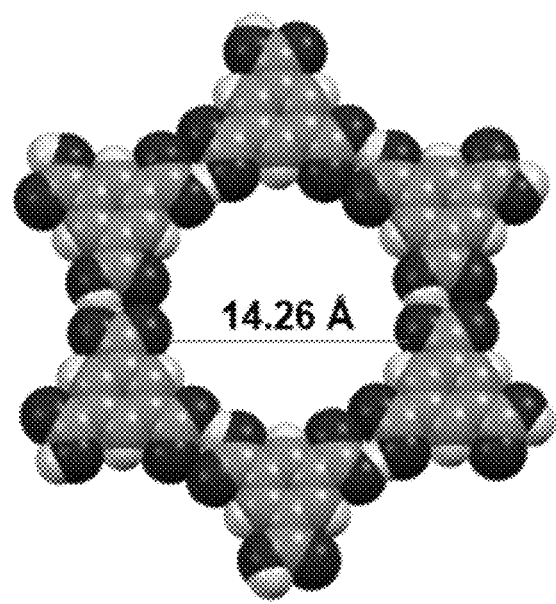
FIG. 2: In single crystal structure of trimesic acid (Form II) six trimesic acid molecules form hexagonal void in the crystal packing with 50% void space and the diameter of the void is about 14.26 Å.

FIG. 2 depicts single crystal structure of trimesic acid (Form II) six trimesic acid molecules form hexagonal void in the crystal packing with 50% void space and the diameter of the void is about 14.26 Å.

Figure 3:
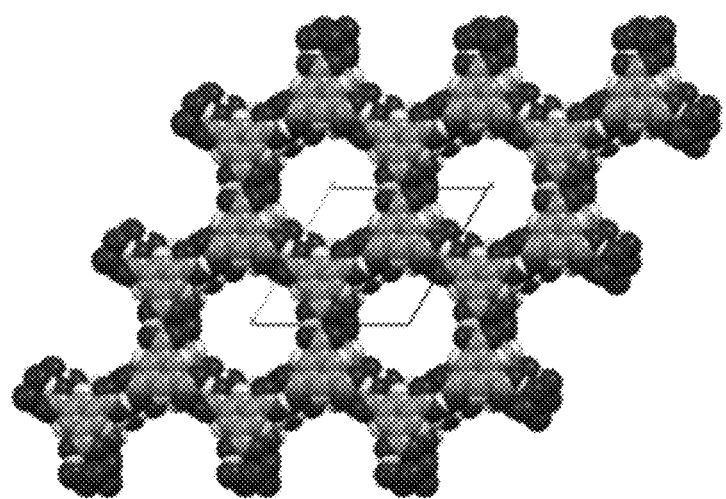
FIG. 3: Form II forms the smallest honeycomb single crystal structure in the nature and hexagonal voids mimics the hollow cylinders which are running along the c-axis. Here 2D along ab plane and 3D extension along c-axis can be seen.

FIG. 3 depicts Form II forms the smallest honeycomb single crystal structure in the nature and hexagonal voids mimics the hollow cylinders which are running along the c-axis. Here 2D along ab plane and 3D extension along c-axis can be seen.

Figure 4:
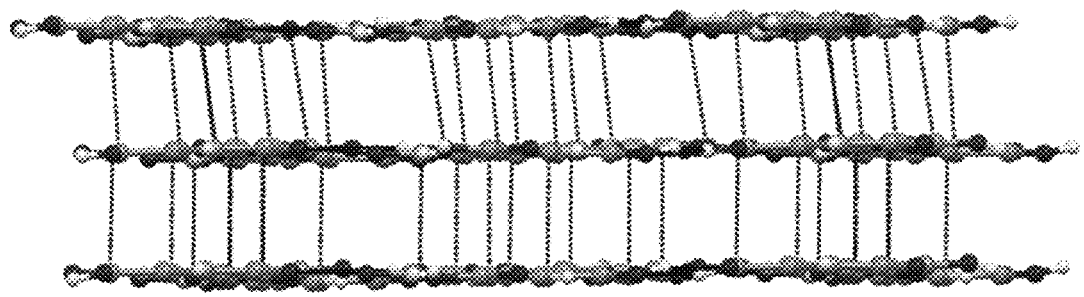
FIG. 4: The π-π stacking of Form II along c-axis.

FIG. 4 depicts the π-π stacking of Form II along c-axis.

FIG. 5 depicts interlocked or interpenetrated structure of trimesic acid (Form I), two different hexagonal rings interpenetrated to form non-porous crystal packing.

Figure 6:
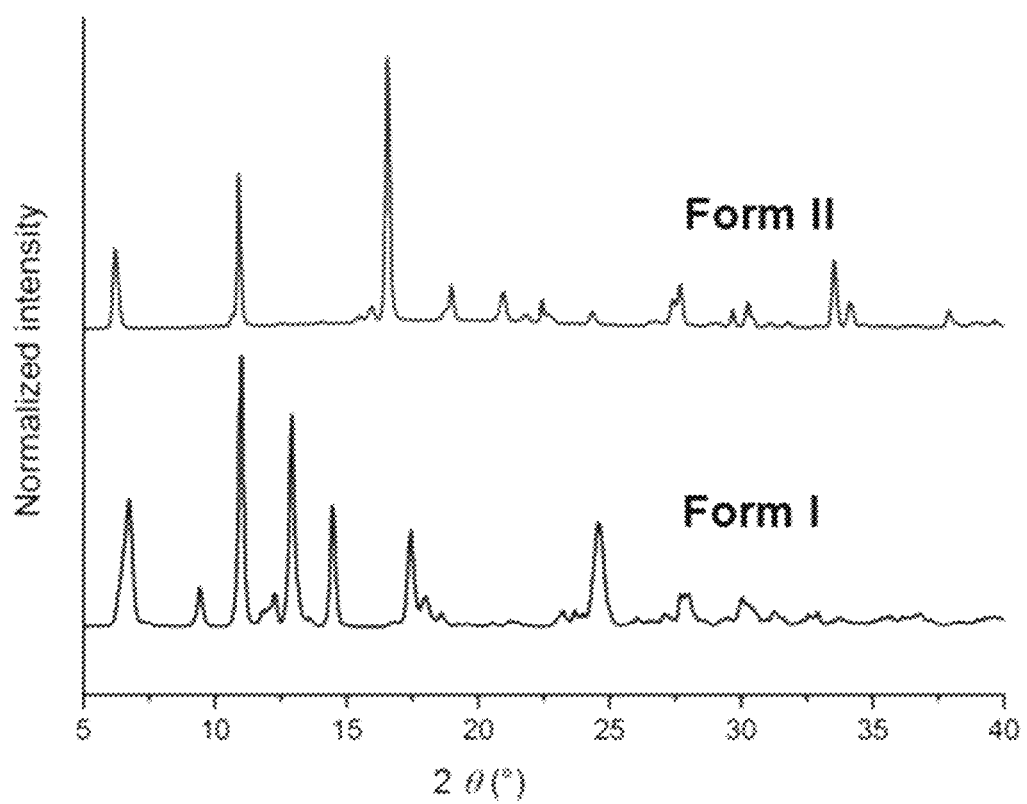
FIGS. 6(a)-6(f): Characterization of trimeric acid Form II (a) PXRD (b) TGA (c) DSC (d) VTSCXRD (e) SSNMR (f) Gas sorption of trimesic acid Form II (to show the porosity).
Figure 6:
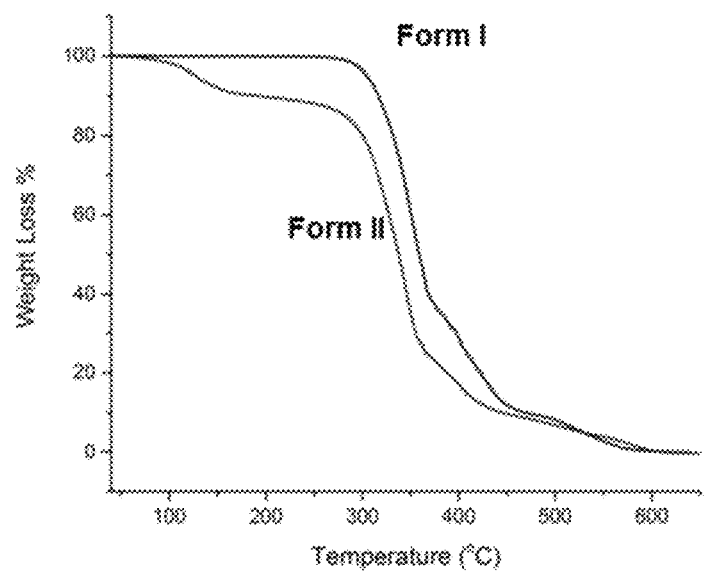
Figure 6:
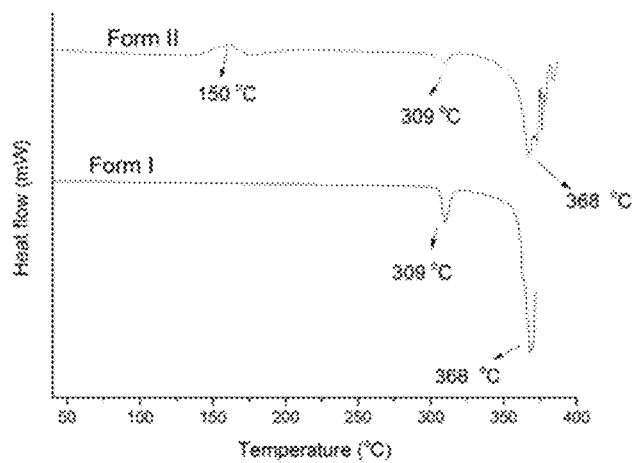
Figure 6:
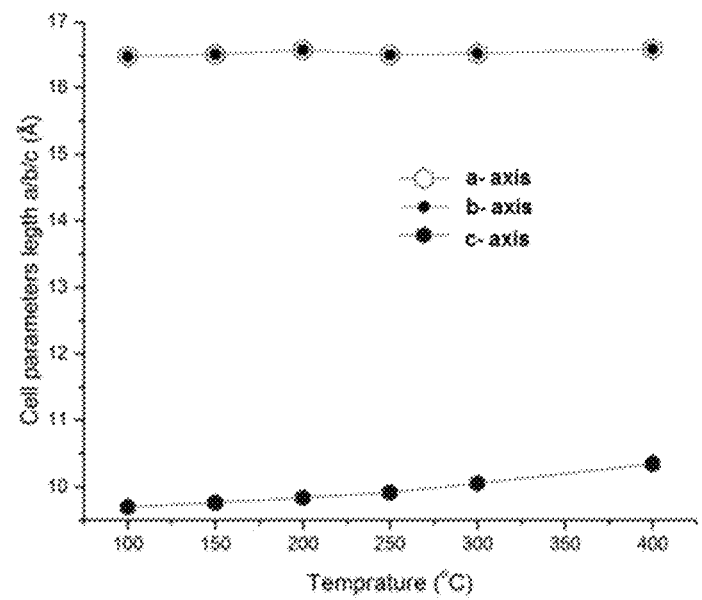
Figure 6:
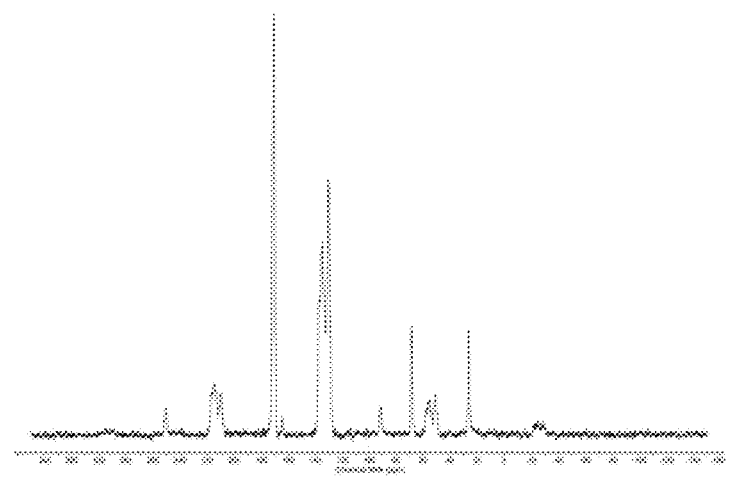
Figure 6:
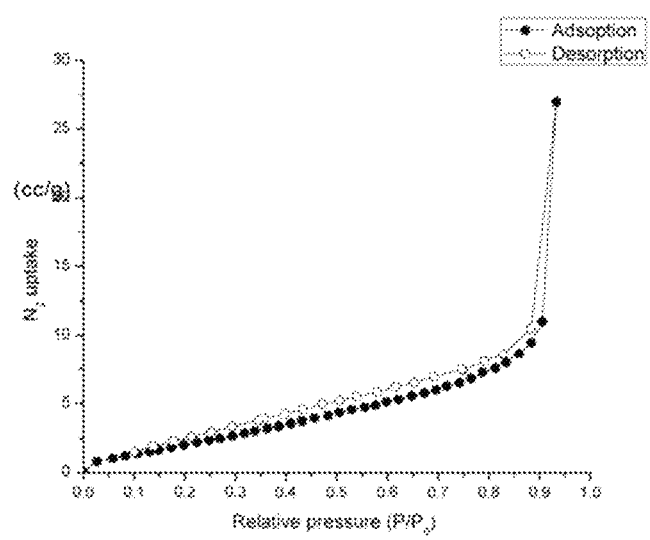

FIG. 6 depicts characterization of trimeric acid Form II (a) PXRD the difference can be noted at 2 θ (°) 6.2 in Form II and 6.7 in Form I and significant peaks (2 θ(°)=12.5 to 15 are missing in Form II. X-ray diffraction pattern of the crystalline Form II of the trimesic acid of Formula (A) having characteristics peaks of 2θ values at 6.2°, 10.9°, 15.5°, 15.9°, 16.6°, 19.0°, 20.9°, 21.9°, 22.5°, 22.8°, 24.4°, 27.4°, 27.9°, 29.7°, 30.3°, 31.1°, 31.9°, 33.6°, 34.4°, 37.9°, 39.1°, 39.7°, 40.7°, 42.6°. (b) TGA Form II shows 10% weight loss at 150° C. (c) DSC Form II show some phase change at 150° C. and finally it melts similar to Form I (d) VTSCXRD also shows with increase in the temperature, a and b axis of unit cell remain constant whereas elongation c-axis can be seen (e) SSNMR (f) Gas absorption of trimesic acid Form II (to show the porosity).

Figure 7:
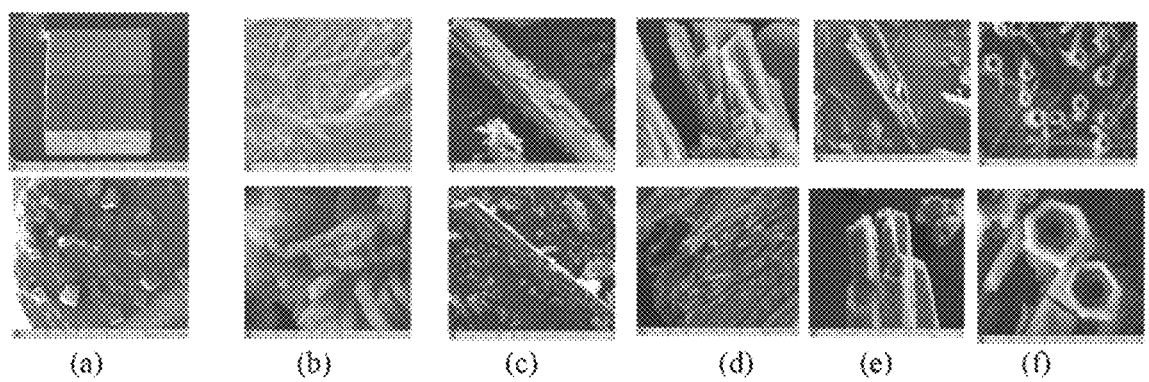
FIG. 7: Morphology evolution in trimesic acid with time (SEM images) (a) TMA Form I (b) TMA Form II 24 hours (c) TMA Form II 48 hours (d) TMA Form II 72 hours (e) TMA Form II 96 hours (f) TMA Form II 120 hours.

FIG. 7 depicts morphology evolution in trimesic acid with time (SEM images).

(a) TMA Form I Morphology looks like block (b) TMA Form II 24 hours, rod shape morphology can be noted and some crystals looks like a block as well as irregular rods (c) TMA Form II 48 hour, rod are formed but perfect hexagonal rods (d) TMA Form II 72 hours, rods started becomes hexagonal type (e) TMA Form II 96 hours, hexanol rods with some voids can be noted (f) TMA Form II 120 hours, hexagonal rods become complete hexagonal hollow cylinders.

Figure 8:
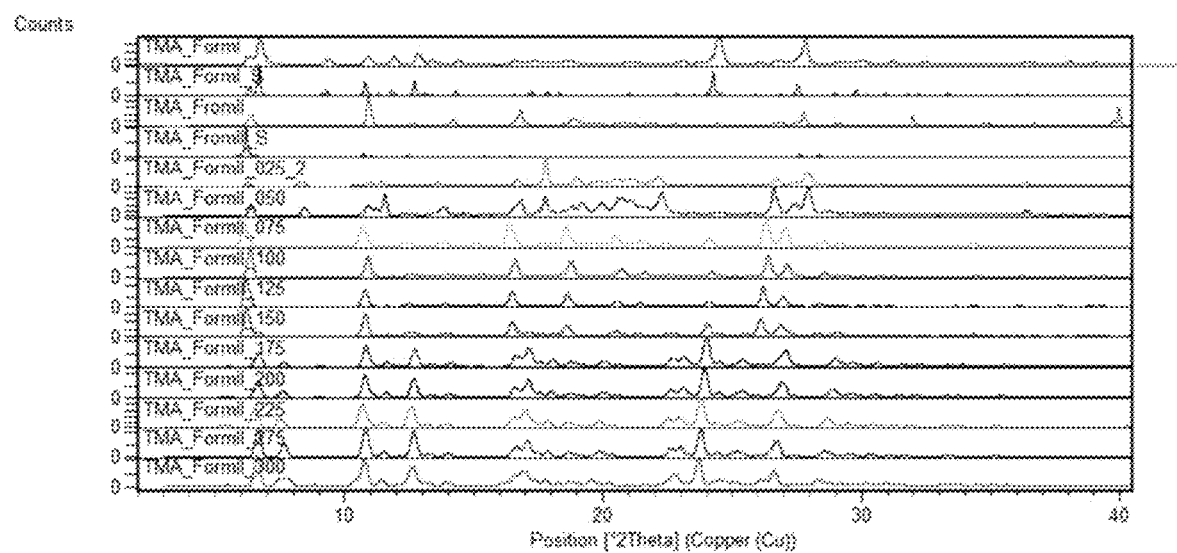
FIG. 8: VT PXRD of trimesic acid Form II compared with Form I (stability).

FIG. 8 depicts VT PXRD of trimesic acid Form II compared with Form I (stability). Form II shows stable in nature.

Figure 9:
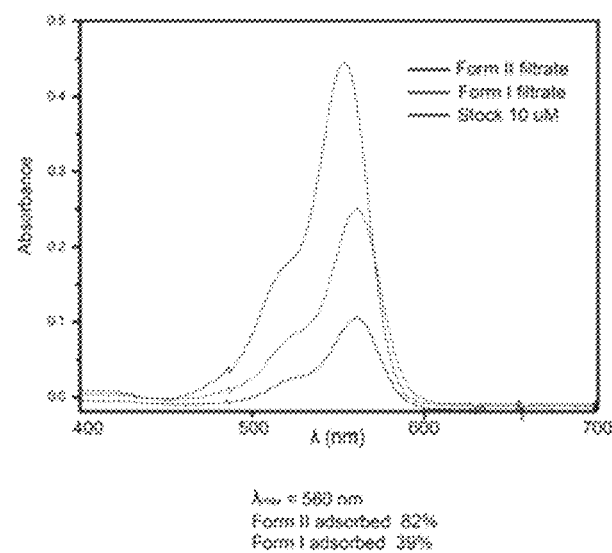
FIG. 9: It shows the absorbance spectra of Form II for Rhodamine B dye.

FIG. 9 shows 82% adsorption for Rhodamine B dye compared to Form I, which shows 39% adsorption.

EXAMPLES

Following examples are given by way of illustration therefore should not be construed to limit the scope of the invention.

Example 1: Synthesis of Single Crystal of Trimesic Acid of Form II 210.14 mg of trimesic acid was dissolved in 5 mL of THF and obtained clear solution. Later, it was kept for slow evaporating at ambient temperature (27° C.). Good quality crystals, hexagonal rods were obtained in 4-5 days.

Example 2: Experimental Procedure

Single crystals were mounted on a Bruker SMART APEX II single crystal X-ray CCD diffractometer having graphite monochromatised (Mo-Kα—0.71073 Å) radiation at low temperature (100K) and 293K. The X-ray generator was operated at 50 kV and 30 mA. The X-ray data acquisition was monitored by APEX2 program suit. The data were corrected for Lorentz-polarization and absorption effects using SAINT and SADABS programs which are integral part of APEX2 package. The structures were solved by direct methods and refined by full matrix least squares, based on F, using SHELXL. Crystal structures were refined using Olex2-1.0 software.

A. Powder X-Ray Diffraction

All crystalline material PXRD data was recorded on a Rigaku, MicroMax-007HF using high-intensity micro focus rotating anode X-ray generator and Cu Kα (α=1.54 Å) radiation source with a Ni filter. Data collection was carried out using an Aluminum holder at a scan speed of 1° min-1 and a step size of 0.02°. All the crystalline material samples were scanned over a range of 2θ=2-40° C. and the corresponding data were collected using Control Win software.

B. Thermal Analysis:

a. Differential Scanning Calorimetry (DSC):

DSC was performed on Mettler-Toledo DSC 822e module, (Mettler-Toledo, Columbus, Ohio). Samples were placed in crimped but vented aluminum pans for DSC experiments. The typical sample size is 3-5 mg for DSC. The temperature range for the heating curves was 30-300° C., and the sample was heated at a rate of 5° C./min. Samples were purged in a stream of dry nitrogen flowing at 80 mL/min.

b. Thermogravimetric Analysis (TGA):

TGA was conducted on a Mettler-Toledo TG50 and SDT Q600 TG-DTA analyzer from 30 to 900° C. under $N_2$ atmosphere with a ramp rate of 10° C. $min^{-1}$.

c. Scanning Electron Microscopy (SEM):

SEM images were recorded on a Zeiss DSM 950 and FEI QUANTA 200 3D microscope equipped with tungsten filament as electron source operated at 10 kV. Samples were directly taken on tape. Prior to the SEM analysis, all the crystalline samples were gold coated using SCD 040 Balzers Union just to avoid sample-charging if there is any during SEM analyses.

d. Nitrogen Adsorption Isotherms:

Nitrogen adsorption isotherms analyses were carried out on Quanta chrome Quadrasorb automatic volumetric instrument at 77 K using liquid nitrogen bath. Prior to gas adsorption treatment samples were degassed at 150° C. for 12 h under vacuum. Surface areas were calculated using Brunauer-Emmett-Teller (BET) model applied between P/PO values of 0.05 S4 and 0.3 for Crystalline TMA. Refer FIG. 6f.

e. Solid-State $^{13}$C:

Solid-state $^{13}$C cross polarization/magic angle spinning (CP/MAS) NMR measurements of TMA were done using Bruker AV 300 NMR at the frequencies 75.47 and 59.63 MHz. As synthesized material of Trimesic acid Form II shows THF in the crystalline material.

Advantages of the Invention

The hexagonal hollow cylinders of porous single crystalline structure of trimesic acid of Form (II) are the smallest honeycomb pattern (hexagon) exits in the nature.

The hexagonal hollow cylinders of porous single crystalline structure of trimesic acid of Form (II) are stable up to 150° C.

Form II shows very high adsorption of Rhodamine B dye, hence may be used to remove Rhodamine B (RHB) dye from wastewater.

The invention claimed is:

1. A hexagonal hollow single crystalline structural Form II of the trimesic acid, wherein the Form II extends two dimensionally without interpenetration of hexagonal rings and extends three dimensionally through π . . . π stacking, wherein the Form II has Formula (A):

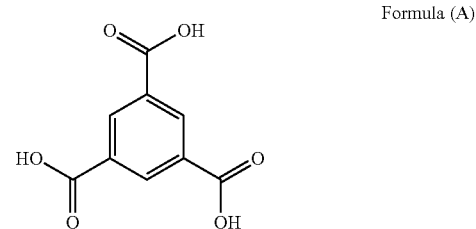 [SMILES: O=C(O)c1cc(C(=O)O)cc(C(=O)O)c1]

Formula (A)

and a powder X-ray diffraction pattern having characteristic peaks of 2θ values at 6.2°, 10.9°, 15.5°, 15.9°, 16.6°, 19.0°, 20.9°, 21.9°, 22.5°, 22.8°, 24.4°, 27.4°, 27.9°, 29.7°, 30.3°, 31.1°, 31.9°, 33.6°, 34.4°, 37.9°, 39.1°, 39.7°, 40.7°, 42.6°.

2. The crystalline structural Form II of the trimesic acid of Formula (A) as claimed in claim 1, wherein said crystalline form is stable up to 150° C.

3. A process for the synthesis of hexagonal hollow single crystalline structural form (Form II) of trimesic acid of Formula (A) as claimed in claim 1, wherein said process comprises of:
 a) dissolving trimesic acid in a suitable solvent to obtain a clear solution; and
 b) evaporating the solution of step (a) at the temperature of 27° C. for 24 to 120 hours to afford hexagonal hollow rods of porous single crystalline structure of trimesic acid.

4. The process for the synthesis of hexagonal hollow single crystalline structural form (Form II) of trimesic acid of Formula (A) as claimed in claim 3, wherein suitable solvent used at step a) for the dissolution of trimesic acid is an ether solvent selected from the group consisting of tetrahydrofuran, diethyl ether, 1,4-dioxane, methyl tert-butyl ether, and mixtures thereof.

5. The crystalline structural Form II of the trimesic acid of Formula (A) as claimed in claim 1 having an 82% adsorption for Rhodamine B (RHB) dye, which has the structure:

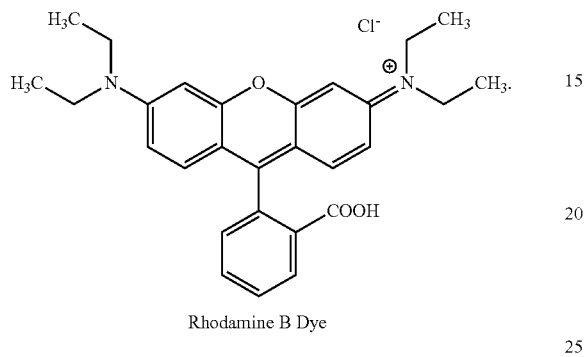

Rhodamine B Dye

* * * * *